United States Patent
Ahn et al.

(10) Patent No.: US 7,166,307 B1
(45) Date of Patent: Jan. 23, 2007

(54) HERB MEDICINE COMPOSITION TO BE SPREAD ON SANITARY NAPKIN FOR FEMALE

(75) Inventors: Deuk Hun Ahn, Taeku (KR); In Jin Baek, Taeku (KR); Tae Hun Ahn, Taeku (KR)

(73) Assignee: Deuk Hun AHN et al., Taeku (KR)

( * ) Notice: Subject to any disclaimer, the term of this patent is extended or adjusted under 35 U.S.C. 154(b) by 0 days.

(21) Appl. No.: 10/030,736

(22) PCT Filed: May 15, 2000

(86) PCT No.: PCT/KR00/00461

§ 371 (c)(1),
(2), (4) Date: May 31, 2002

(87) PCT Pub. No.: WO01/03748

PCT Pub. Date: Jan. 18, 2001

(30) Foreign Application Priority Data

Jul. 13, 1999 (KR) .............................. 1999-28248

(51) Int. Cl.
*A61K 36/00* (2006.01)

(52) U.S. Cl. ...................... 424/725; 424/404; 424/411; 424/443; 424/740

(58) Field of Classification Search ................ 424/725, 424/430, 58, 404, 411, 443, 740
See application file for complete search history.

(56) References Cited

U.S. PATENT DOCUMENTS

| 5,079,004 A | * | 1/1992 | Blank et al. | ................ 424/404 |
| 5,466,452 A | * | 11/1995 | Whittle | ....................... 424/750 |
| 5,837,257 A | * | 11/1998 | Tsai et al. | .................... 424/741 |
| 5,877,298 A | * | 3/1999 | Fahim et al. | ............... 530/412 |

OTHER PUBLICATIONS

Ahn, Y. et al. "Growth-inhibitory effects of Galla Rhois-derived tannins on intestinal bacteria," 1998, Journal of Applied Microbiology, (84), pp. 439-443.*

* cited by examiner

Primary Examiner—Christopher Tate
Assistant Examiner—S. B. McCormick-Ewoldt
(74) Attorney, Agent, or Firm—Mayer Brown Rowe & Maw LLP

(57) ABSTRACT

The present invention relates to a Galla Rhois-containing composition to be spread on sanitary napkin for female. Preferably, the present invention further comprises one or more herb medicine selected from a group consisting of *Artemisia* Folia, Sophorae, *flavescens*, Phellodendri Cortex, *Torilis anthriscus* and alum.

4 Claims, 1 Drawing Sheet

HERB MEDICINE COMPOSITION TO BE SPREAD ON SANITARY NAPKIN FOR FEMALE

TECHNICAL FIELD

The present invention relates to a composition to be spread on sanitary napkin for female, and more specifically relates to an herb medicine extracts-containing composition to be spread on female sanitary napkin, which can be spread on female napkin in order to remove odious smell and itch occurring at the period of menses.

BACKGROUND ART

Although the amount of menstrual flow differs depending on individual female, it normally amounts to 100 to 300 cc and the amount of pure blood thereof is 30 to 50 cc, and various exudates such as cervical mucus or vulval sebaceous glands and fused endosporium are mixed, so even healthy female has peculiar smell due to the exudates.

Female sanitary napkin currently used is pads having simple function of absorbing menstrual flow by adopting different thickness depending on the amount of menstrual flow, but could not eliminate the peculiar smell and itch at the period. Most of female sanitary napkins do not allow leakage of moisture by exterior vinyl cover, and this is the same as window-blocked bathroom, thus likely to result in fungal or bacterial multiplication. Further, the smell peculiar to menstrual flow that female should endure since menarche to menopause for several decades is a main cause for the restriction of female activities.

The inventors of the present invention have conducted extensive studies to remove the smell and itch at the period and finally discovered the fact that the smell and itch could be prevented by preparing pads made from cotton cloth or paper sheet on which medicinal substance was spread, due to the effect of the medicine incorporated, and based on this, completed the present invention.

Therefore, the object of the present invention is to provide a composition to be spread on female sanitary napkin, which basically prevents itch at skin contact region and smell of menstrual blood by using harmless herb medicine.

DISCLOSURE OF INVENTION

The present invention is directed to a Ghalla Rhois-containing composition to be spread on female sanitary napkin.

Specifically, the present invention relates to an herb medicine composition that can be applied to female sanitary napkin to prevent smell, specifically composition to be spread on female sanitary napkin, which contains as main component Ghalla Rhois having antibacterial and antiseptic effect.

According to disclosures in Korean Pharmacopoeia and the conventional medical references, Galla Rhois contains 70% of tannin and starch, exhibits a strong astringency, leading to dryness of mucous membrane due to suppression of cellular secretion, thus used in treatment of diarrhea, bleeding, hysterorrhea and stomatitis. For external use, it is used for womb bleeding and genital diseases via powder spread or decoction. Further, tannin component affects nutrition and metabolism of bacteria by solidifying protein, thus exhibits antibiotic and antiseptic effect, and can be used as antidote against alkaloid poisoning.

Though the composition in the present invention can accomplish the intended purpose even when Galla Rhois is contained alone, it is more preferred to contain one or more herb medicine selected from a group consisting of *Artemisia* Folia, Sophorae *flavescens*, Phellodendri Cortex, *Torilis anthriscus* and alum, and at this time, the content is 25–98% by weight of Galla Rhois, 2–30% by weight of *Artemisia* Folia, 2–30% by weight of Sophorae *flavescens,* 10–50% by weight of Phellodendri cortex, 1–20% by weight of *Torilis anthriscus* and 10–40% by weight of alum, respectively, based on total dried weight of the composition. It is more preferred to contain *Artemisia* Folia, Phellodendri Cortex, *Torilis anthriscus* and alum besides Galla Rhois, or Sophorae *flavescens*, Phellodendri cortex, *Torilis anthriscus* and alum together with Galla Rhois.

According to the description in the Korean Pharmacopoeia and the conventional oriental medicine references, *Artemisia* Folia is used in the treatment of gynecopathy such as menstrual irregularity and hysterorrhea, and shows antibacterial activity against gonococcus etc. and externally used in treating eczema and pruritis.

In addition, Sophorae *flavescens* is mainly used for external use due to its bitter taste, and used clinically as cataplasm or detergent in treatment of skin disease with serious itch and eczema, skin pyosis because of its anti-trichomonas activity.

Additionally, Phellodendri Cortex has germicidal activity against *E. coli*, typhus and cholera *bacilli* and antibacterial effect against Gram-positive, Gram-negative and gonococcus. Among the ingredients of Phellodendri Cortex, Berberin shows a strong local astringency and is effective for removal of heat toxicity of wound region when externally used for prunitic skin diseases.

Also, *Torilis anthriscus* has drying effect for dampness and germicidal effect, thus it is externally used, in form of powder or decoction, as detergent in the treatment of vulvar pruritis.

Further, alum has a strong astringency, antibacterial activity and anti-pruritis activity, thereby gives freshness to inflammatory region by removing discomfort and bad smell. Thus, it is mainly used for external use as an astringent in inflammation of skin mucous membrane or as gargles for the purpose of local astringency.

Herb medicines enumerated above, that is, Galla Rhois, *Artemisia* Folia, Sophorae *flavescens*, Phellodendri Cortex, *Torilis anthriscus* and alum all exhibit antibiotic and anti-pruritis effect while being harmless to human, thus frequently used clinically. They have strong antibiotic, astringent activity and antiseptic activity, so rapidly eliminates odious smell and itch at the period, further prevents dampness of genital region during the period due to their unique cold properties.

Galla Rhois, *Artemisia* Folia, Sophorae *flavescens*, Phellodendri Cortex, *Torilis anthriscus* and alum can, respectively, provide the composition to be spread on female sanitary napkin as a type selected from powder, extracts and infusion. For example, effective component of said herb medicines can be extracted with water and can be used by mixing with alum extracts.

The composition of the present invention can be formulated into powders, liquids, suspensions or gels with pharmaceutically accepted carrier depending on physico-chemical properties of the active substance, further the composition of the present invention can further contain other additives. Liquid formulation is particularly preferred from the viewpoint of utility, but if necessary, other formulation such as powders, spray, gels etc. may be adopted.

Another embodiment of the present invention is a female sanitary napkin to which the composition of the present invention was applied. The composition of the present invention can be uniformly applied to overall absorbent matrix of sanitary napkin. However, there is a disadvantage that the absorbency of the absorbent matrix itself is decreased. It is preferable to spread, not on matrix itself, only on upper surface of matrix, that is, the surface through which menstrual blood should pass when absorbed into matrix, thereby allowing the menstrual flow to be absorbed into matrix while being mixed with the composition of the present invention. As an example, a primary pad where the composition of the present invention was sufficiently spread on cotton cloth or paper sheet can be put on conventional sanitary napkin.

As another way to apply the composition of the present invention, the composition, in powder form, is uniformly distributed through whole sanitary napkin, thereby mixed with menstrual flow without effect on absorbency of matrix itself.

The composition of the present invention can be applied in any route as long as it allows mixing menstrual blood with the composition of the present invention and does not decrease absorbency of matrix itself.

EXAMPLE

Figure 1:
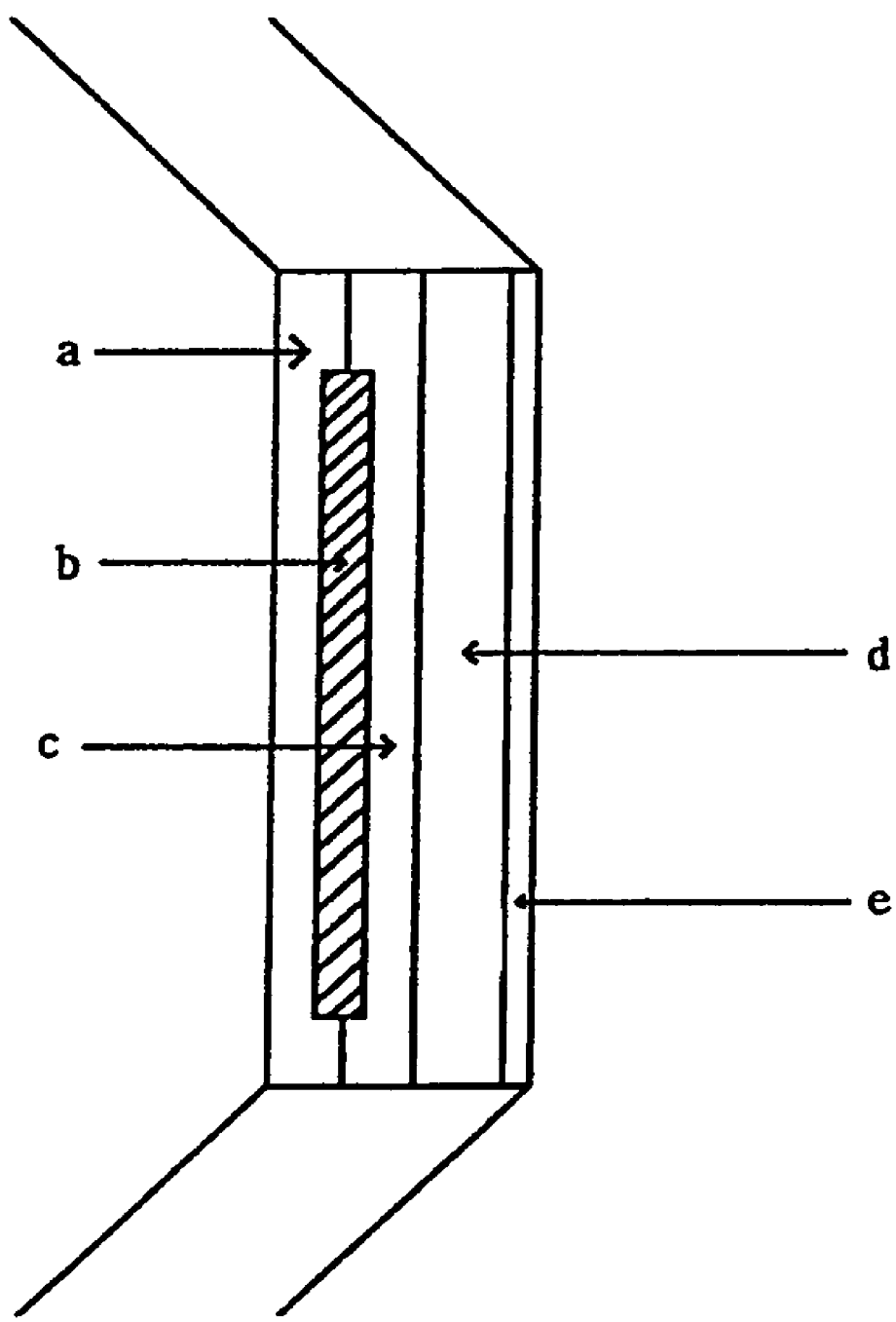
FIG. 1 is a cross sectional view for Application Example 6 as an example for female sanitary napkin to which the composition of the present invention was applied. Herein, a and c are polypropylene membrane, b is primary pad, d is absorbent matrix and e is vinyl cover.

The present invention is more specifically explained by the following Examples and Experimental Examples, but is not limited thereby.

Example 1

Preparation of Composition to be Spread on Female Sanitary Napkin 800 g of Galla Rhois was washed with distilled water, and put into a 5000 ml round bottom flask. 2000 ml of distilled water was added thereto, and condenser was attached and extraction was conducted by heating for 2 hours. Extracts was filtered by filter cloth and the filtrate was subjected to vacuum concentration to obtain viscous extract 1000 ml.

Example 2

Preparation of Composition to be Spread on Female Sanitary Napkin 600 g of Galla Rhois was washed with distilled water, put into 5000 ml round bottom flask together with 200 g of alum, mixed with 2000 ml of distilled water, attached to condenser and extracted by heating for 2 hours. Extracts was filtered by filter cloth And the filtrate was subjected to vacuum concentration to form viscous extract, 1000 ml.

Example 3

Preparation of Composition to be Spread on Female Sanitary Napkin 760 g of Galla Rhois and 40 g of *Artemisia* Folia were washed with distilled water, put into 5000 ml round bottom flask, mixed with 2000 ml of distilled water, attached to condenser, and extracted for 2 hours. Extract was filtered with filter cloth and this filtrate was subjected to vacuum concentration to obtain viscous extract 1000 ml.

Example 4

Preparation of Composition to be Spread on Female Sanitary Napkin 640 g of Galla Rhois and 160 g of Phellodendri Cortex were washed with distilled water, put into 5000 ml round bottom flask, mixed with 2000 ml of distilled water, attached to condenser, and extracted for 2 hours. Extract was filtered with filter cloth and this filtrate was subjected to vacuum concentration to obtain viscous extract 1000 ml.

Example 5

Preparation of Composition to be Spread on Female Sanitary Napkin

A) 300 g of Galla Rhois, 100 g of Sophorae *flavescens*, 150 g of Phellodendri Cortex, 50 g of *Torilis anthriscus* and 100 g of alum were washed with distilled water, put into 5000 ml round bottom flask, mixed with 2000 ml of distilled water, attached to condenser, and extracted for 2 hours. Extract was filtered with filter cloth and this filtrate was subjected to vacuum concentration to obtain viscous extract 500 ml.

B) 100 g of alum was pulverized, precipitated in 500 ml of purified water at 75–80° C. for 2 hours and filtered. This was mixed with viscous extract obtained in A) by 1:1 ratio to prepare crude liquid.

Example 6

Preparation of Composition to be Spread on Female Sanitary Napkin

A) 30 kg of Galla Rhois, 10 kg of *Artemisia* Folia, 24 kg of Phellodendri Cortex, 2 kg of *Torilis anthriscus* and 5 kg of alum were washed with distilled water, put into a dual tank—container with 1200 L of purified water, heated for 8 hours at 95–100° C. and the extract obtained was filtered. The filtrate was moved to storage bath of the dual tank and filtered, and subjected to vacuum concentration at 60° C. to obtain 40 L of viscous extract.

B) 5 kg of alum was pulverized, precipitated in 40 L of purified water at 75–80° C. for 2 hours and filtered. This was mixed with the viscous extract obtained in A) by 1:1 ratio to prepare crude liquid.

Application Examples 1–5

Preparation of Primary Pad

Each napkin tissue made of natural pulp of 14×5 cm was soaked into the composition prepared from said Examples 1–5 respectively. Thus, per 1 tissue, 0.25 g (based on dried weight) of the formulation was uniformly spread on. These were dried to prepare primary pads.

Application Examples 6–10

Preparation of Sample Pads

The primary pads prepared from Application Examples 1–5 were, respectively, inserted between two layers of 100% polypropylene for diaper, and were subjected to heat treatment. These were put onto conventional sanitary napkin as shown in FIG. 1.

Application Example 11

Preparation of Sanitary Napkin

The composition prepared from Example 6 was spread on a woven cloth of 12 cm (width)×4000 m (length), which is used for female sanitary napkin, to allow uniform spread, i.e. about 1 g, as dried weight, of the composition on a pad of 21 cm×9 cm. By using the woven cloth spread, pulp and absorbent structure together, sanitary napkin of 21 cm×9 cm was prepared at a factory currently producing sanitary napkin.

Experimental Example 1

Experiment for Confirming Toxicity and Negative Effect

The composition prepared in said Example 5 was spread on vaginal orifice of 4 mature female rabbit five times, every 20 minutes, and observed every hour for 6 hours. Further, 6 ml of the composition was daily spread for continuous 5 days and observed.

As the result of the spread of the composition of the present invention, no deterioration of surface in genital organ or no histological change was observed except contraction of vaginal orifice.

Experimental Example 3

Confirmation Experiment II for Toxicity and Negative Effects

Two persons were selected among the families of the inventors of the present invention, and sample pad prepared from Application Example 10 was attached on the conventional sanitary napkin, which they had used for past three months, and reaction at skin contact was observed.

As the result, no change in skin tissue or local negative reaction was observed by the use of the pad on which the composition of the present invention was spread. However, it was observed that once menstrual blood is absorbed into pad, the color was turned to black, and this phenomenon was due to mixing of menstrual blood with medicine spread on the pad. This was inferred as main mechanism of preventing bad smell and itch, the purpose of the present invention.

Experimental Example 3

Efficacy Experiment Against Odious Smell of Menstrual Flow and Itch

Sample pads prepared from Application Examples 6, 7 and 10, to which the compositions of Examples 1, 2 and 5 were applied respectively, were used to conduct efficacy experiment. All the female subject had smell and itch, but no particular organic physical disorder. Supposing that each person consumes 5 pads daily, pads enough for 6 days were given to each subject. The subject was made to report the result simultaneously with the end of menses. All the subject reported the result after about one month and the result is as shown in Tables 1–6.

TABLE 1

Experimental result for Application Example 6

| Age | Number of Subject | Subject recognizing suppressive effect for smell ||||| 
|---|---|---|---|---|---|---|
| | | No effect | 30% suppression | 50% suppression | 70% suppression | 90% suppression |
| 10–19 | 2 | 0 | 0 | 1 | 1 | 0 |
| 20–29 | 6 | 0 | 1 | 3 | 1 | 1 |
| 30–39 | 4 | 0 | 1 | 1 | 2 | 0 |
| 40–49 | 2 | 0 | 1 | 1 | 0 | 0 |
| Total (%) | 14 | 0 | 3 (21.4%) | 6 (42.9%) | 4 (28.6%) | 1 (7.1%) |

TABLE 2

Experimental Result for Application Example 6

| Age | Number of Subject | Subject recognizing suppressive effect for itch ||||| 
|---|---|---|---|---|---|---|
| | | No effect | 30% suppression | 50% suppression | 70% suppression | 90% suppression |
| 10–19 | 2 | 0 | 0 | 2 | 0 | 0 |
| 20–29 | 6 | 0 | 2 | 4 | 0 | 0 |
| 30–39 | 4 | 0 | 1 | 2 | 1 | 0 |
| 40–49 | 2 | 0 | 0 | 2 | 0 | 0 |
| Total (%) | 14 | 0 | 3 (21.4%) | 10 (71.4%) | 1 (7.1%) | 0 |

TABLE 3

Experimental Result for Application Example 7

| Age | Number of Subject | Subject recognizing suppressive effect for smell ||||| 
|---|---|---|---|---|---|---|
| | | No effect | 30% suppression | 50% suppression | 70% suppression | 90% suppression |
| 10–19 | 2 | 0 | 0 | 0 | 2 | 0 |
| 20–29 | 10 | 0 | 1 | 3 | 5 | 1 |
| 30–39 | 6 | 0 | 0 | 1 | 4 | 1 |
| 40–49 | 2 | 0 | 0 | 1 | 1 | 0 |
| Total (%) | 20 | 0 | 1 (5.0%) | 5 (25.0%) | 12 (60.0%) | 2 (10.0%) |

TABLE 4

Experimental Result for Application Example 7

| Age | Number of Subject | Subject recognizing suppressive effect for itch ||||| 
|---|---|---|---|---|---|---|
| | | No effect | 30% suppression | 50% suppression | 70% suppression | 90% suppression |
| 10–19 | 2 | 0 | 0 | 0 | 1 | 1 |
| 20–29 | 10 | 0 | 1 | 3 | 6 | 0 |
| 30–39 | 6 | 0 | 0 | 2 | 2 | 2 |
| 40–49 | 2 | 0 | 0 | 1 | 1 | 0 |
| Total (%) | 20 | 0 | 1 (5.0%) | 6 (30.0%) | 10 (50.0%) | 3 (15.0%) |

TABLE 5

Experimental Result for Application Example 10

Number Subject recognizing suppressive effect for smell

| Age | of Subject | No effect | 30% suppression | 50% suppression | 70% suppression | 90% suppression |
|---|---|---|---|---|---|---|
| 10–19 | 1 | 0 | 0 | 1 | 0 | 0 |
| 20–29 | 8 | 0 | 0 | 1 | 5 | 2 |
| 30–39 | 2 | 0 | 0 | 0 | 1 | 1 |
| 40–49 | 1 | 0 | 0 | 1 | 0 | 0 |
| Total (%) | 12 | 0 | 0 | 3 (25.0%) | 6 (50.0%) | 3 (25.0%) |

TABLE 6

Experimental Result for Application Example 10

Number Subject recognizing suppressive effect for itch

| Age | of Subject | No effect | 30% suppression | 50% suppression | 70% suppression | 90% suppression |
|---|---|---|---|---|---|---|
| 10–19 | 1 | 0 | 0 | 0 | 0 | 1 |
| 20–29 | 8 | 0 | 2 | 3 | 2 | 1 |
| 30–39 | 2 | 0 | 0 | 2 | 0 | 0 |
| 40–49 | 1 | 0 | 0 | 0 | 1 | 0 |
| Total (%) | 12 | 0 | 2 (16.7%) | 5 (41.7%) | 3 (25.0%) | 2 (16.7%) |

In the experiment for Application Example 6 adopting the composition of Example 1, 78.6% of subject reported at least 50% suppressive effect against both smell (Table 1) and itch (Table 2).

In the experiment for Application Example 7 adopting the composition of Example 2, 95.0% of subject reported at least 50% suppressive effect against smell (Table 3) and itch (Table 2).

Furthermore, in the experiment for Application Example 10 adopting the composition of Example 5, the entire subject reported at least 50% of suppressive effect for smell (Table 5), and in particular, even 3 persons (25.0% of subject) hardly experienced any smell (i.e. reported at least 90% suppressive effect). Further, in case of the suppressive effect for itch shown in Table 6, 83.3% of subject reported at least 50% suppressive effect.

There was no negative effect observed, except for the change in menstrual blood, after using the pad according to the present invention.

Experimental Example 4

Comparative Experiment for Suppressive Effect for Smell and Itch

With regard to smell suppression effect, a comparative experiment was conducted for the sanitary napkin adopting the composition of the present invention, and also for two kinds of sanitary napkins (A company product and B company product) that are advertised as being effective against smell.

As the sanitary napkin using the composition of the present invention, sanitary napkin in Application Example 11 adopting the composition of Example 6 was used. A total of 20 subject were randomly selected among the female who agreed to the comparative experiment. Survey item on efficacy of sanitary napkin was established and survey paper was prepared in advance so that the subject could fully understand the items, and gave a total of 30 sanitary napkins, 10 for each kind, to each person. Survey item was composed of 1) smell suppression effect, 2) itch suppression effect and 3) other opinion after using the pad, and the result was made to be reported simultaneously with the end of menses.

As the result, it could be confirmed that both A product and B product exhibited no suppressive effect (90% of subject) or trivial effect (10% of subject) against smell, while in contrast, the sanitary napkin adopting the composition of the present invention exhibited obvious suppressive effect (all subject) for smell and even for itch.

Experimental Example 5

General Consumer Test on the Effect of Suppressing Smell of Menstrual Blood and Itch 60 persons were randomly selected among female who are in age of 13 to 49 and live in Seoul, Chungju and Daeku, Korea, and let them using the sanitary napkin adopting the composition of the present invention to test the efficacy. As the sanitary napkin using the composition of the present invention, female sanitary napkin in Application Example 11 adopting the composition in Example 6 was employed.

Among the subject, 95% or more admitted that the smell suppression effect was superior (at least 70% suppression effect) or significant (suppression effect of at least 25%). Concerning itch suppression effect, except for 15% subject who had never experienced itch, most of the subject acknowledged the existence of superior (67% of subject) or significant (18% of subject) itch suppression effect.

Further, as result of using the sanitary napkin adopting the composition of the present invention, a majority of female confirmed the fact that menstrual blood did not spread out and that they did not experience dampness at the skin contact, and in particular, in case of female who has to use sanitary napkin through month due to abnormal menses (bleeding), it could be confirmed that there was neither skin sore nor smell. This was due to unique properties of herb medicine in the present invention, i.e., removal of dampness and astringency, and becomes another important advantage of the present invention in addition to the smell and itch suppression.

Additionally, even in actual consumer test, none of the subject exhibited negative effect at the skin contact.

The female sanitary napkin on which composition of the present invention is spread, which is prepared by using natural drug substance exhibiting treatment efficacy while being harmless to human, suppresses itch at the skin contact and odious smell of menstrual blood, which could not be resolved by the conventional sanitary napkin, thus prevents restriction in activities due to smell, allows female to lead more active life and basically makes female free. Further, the composition of the present invention can be applied by spreading to conventional woven cloth used for sanitary napkin currently, thus it is industrially valuable.

The invention claimed is:

1. A composition to be spread on sanitary napkins for females comprising an aqueous extract of Galla Rhois and an aqueous extract of *Artemisia* Folia.

2. The composition in claim 1, which further comprises one or more components selected from a group consisting of an aqueous extract of Sophorae *flavescens*, an aqueous extract of Phellodendri Cortex, an aqueous extract of *Torilis anthriscus* and alum;

wherein the aqueous extract of Galla Rhois is in an amount of 25–98% by weight, the aqueous extract of *Artemisia* Folia is in an amount of 2–30% by weight, the aqueous extract of Sophorae *flavescens* is in an amount of 2–30% by weight, the aqueous extract of Phellodendri Cortex is in an amount of 10–50% by weight, the aqueous extract of *Torilis anthriscus* is in an amount of 1–20% by weight and Alum is in an amount of 10–40% weight based on the total dry weight of the composition.

3. The composition in claim 2, which comprises an aqueous extract of Galla Rhois, an aqueous extract of *Artemisia* Folia, an aqueous extract of Phellodendri Cortex, an aqueous extract of *Torilis anthriscus* and alum.

4. A sanitary napkin comprising the composition according to claim 2.

* * * * *